(12) United States Patent
Hoernschemeyer et al.

(10) Patent No.: US 12,082,849 B2
(45) Date of Patent: Sep. 10, 2024

(54) DUAL TETHER SUPPORT OF VERTEBRA

(71) Applicant: OrthoPediatrics Corp., Warsaw, IN (US)

(72) Inventors: Daniel Gerard Hoernschemeyer, Columbia, MO (US); Matthew Prygoski, North Liberty, IN (US); Rick Detlefsen, Warsaw, IN (US); Evangelos Tozakoglou, Fort Wayne, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 1098 days.

(21) Appl. No.: 16/845,653

(22) Filed: Apr. 10, 2020

(65) Prior Publication Data

US 2020/0323562 A1 Oct. 15, 2020

Related U.S. Application Data

(60) Provisional application No. 62/832,943, filed on Apr. 12, 2019.

(51) Int. Cl.
*A61B 17/70* (2006.01)

(52) U.S. Cl.
CPC ...... *A61B 17/7022* (2013.01); *A61B 17/7023* (2013.01); *A61B 17/7032* (2013.01)

(58) Field of Classification Search
CPC .............. A61B 17/7019; A61B 17/702; A61B 17/7022; A61B 17/7026; A61B 17/7029; A61B 17/7031; A61B 17/7053; A61B 17/7007; A61B 17/7044; A61B 17/842; A61B 17/7049; A61B 17/7041; A61B 17/7043; A61B 17/7058; A61B 17/0642; A61B 17/70–7059

See application file for complete search history.

(56) References Cited

U.S. PATENT DOCUMENTS

| | | |
|---|---|---|
| 3,997,138 A | 12/1976 | Crock et al. |
| 4,773,402 A | 9/1988 | Asher et al. |
| 5,330,473 A | 7/1994 | Howland |
| 5,387,213 A | 2/1995 | Beard et al. |

(Continued)

FOREIGN PATENT DOCUMENTS

WO  WO-2013116150 A1 *  8/2013  ......... A61B 17/7032

*Primary Examiner* — Lynnsy M Summitt
(74) *Attorney, Agent, or Firm* — Gerald W. Roberts; John V. Daniluck; Dentons Bingham Greenebaum LLP

(57) ABSTRACT

An apparatus includes a first flexible connector and a second flexible connector. The apparatus also includes a first bone anchor including a first tethering head configured to receive a first portion of the first flexible connector. The apparatus also includes a second bone anchor including a second tethering head configured to receive a second portion of the first flexible connector. The apparatus also includes a third bone anchor defining a first aperture configured to receive therethrough the first bone anchor. The third bone anchor also defines a first peripheral channel configured to receive a first portion of the second flexible connector. The apparatus also includes a fourth bone anchor defining a second aperture configured to receive therethrough the second bone anchor. The fourth bone anchor also defines a second peripheral channel configured to receive a second portion of the second flexible connector.

12 Claims, 10 Drawing Sheets

(56) References Cited

U.S. PATENT DOCUMENTS

| | | | | |
|---|---|---|---|---|
| 5,603,714 | A * | 2/1997 | Kaneda | A61B 17/7034 606/272 |
| 5,702,395 | A * | 12/1997 | Hopf | A61B 17/7044 606/265 |
| 6,132,431 | A | 10/2000 | Nilsson et al. | |
| 6,206,879 | B1 | 3/2001 | Marnay et al. | |
| 6,488,683 | B2 * | 12/2002 | Lieberman | A61B 17/701 606/279 |
| 6,533,787 | B1 * | 3/2003 | Lenke | A61B 17/7044 606/75 |
| 7,572,277 | B2 | 8/2009 | Roussouly | |
| 7,803,174 | B2 | 9/2010 | Denis et al. | |
| 8,034,085 | B2 * | 10/2011 | Slivka | A61B 17/7044 606/270 |
| 8,361,130 | B2 | 1/2013 | Daly et al. | |
| 8,414,616 | B2 * | 4/2013 | Berrevoets | A61B 17/809 606/297 |
| 8,506,602 | B2 | 8/2013 | Slivka | |
| 8,518,085 | B2 | 8/2013 | Winslow et al. | |
| 8,657,857 | B2 | 2/2014 | Dall et al. | |
| 8,795,336 | B2 * | 8/2014 | Biedermann | A61B 17/702 606/267 |
| 9,060,815 | B1 | 6/2015 | Gustine et al. | |
| 9,241,739 | B2 | 1/2016 | Mueller et al. | |
| 9,345,517 | B2 | 5/2016 | Zhang et al. | |
| 9,402,666 | B2 * | 8/2016 | Al Shail | A61B 17/7059 |
| 9,439,679 | B2 | 9/2016 | Dall et al. | |
| 9,510,862 | B2 | 12/2016 | Montello et al. | |
| 9,517,089 | B1 | 12/2016 | Casey et al. | |
| 9,579,126 | B2 | 2/2017 | Zhang et al. | |
| 9,579,131 | B1 | 2/2017 | Gustine et al. | |
| 9,615,867 | B2 | 4/2017 | Picetti et al. | |
| 9,848,915 | B2 * | 12/2017 | Beger | A61B 17/7032 |
| 9,949,763 | B2 * | 4/2018 | Rezach | A61B 17/705 |
| 9,980,755 | B2 | 5/2018 | Murray et al. | |
| 10,188,431 | B2 | 1/2019 | Erbulut et al. | |
| 10,420,590 | B2 * | 9/2019 | Le Couëdic | A61B 17/7067 |
| 10,426,527 | B2 | 10/2019 | Doose et al. | |
| 10,624,679 | B2 | 4/2020 | Murray et al. | |
| 2004/0111088 | A1 | 6/2004 | Picetti et al. | |
| 2005/0171537 | A1 | 8/2005 | Mazel et al. | |
| 2008/0058805 | A1 | 3/2008 | Stuart | |
| 2019/0059949 | A1 * | 2/2019 | Ziemek | A61B 17/809 |
| 2022/0110662 | A1 * | 4/2022 | LaColla | A61B 17/7044 |

* cited by examiner

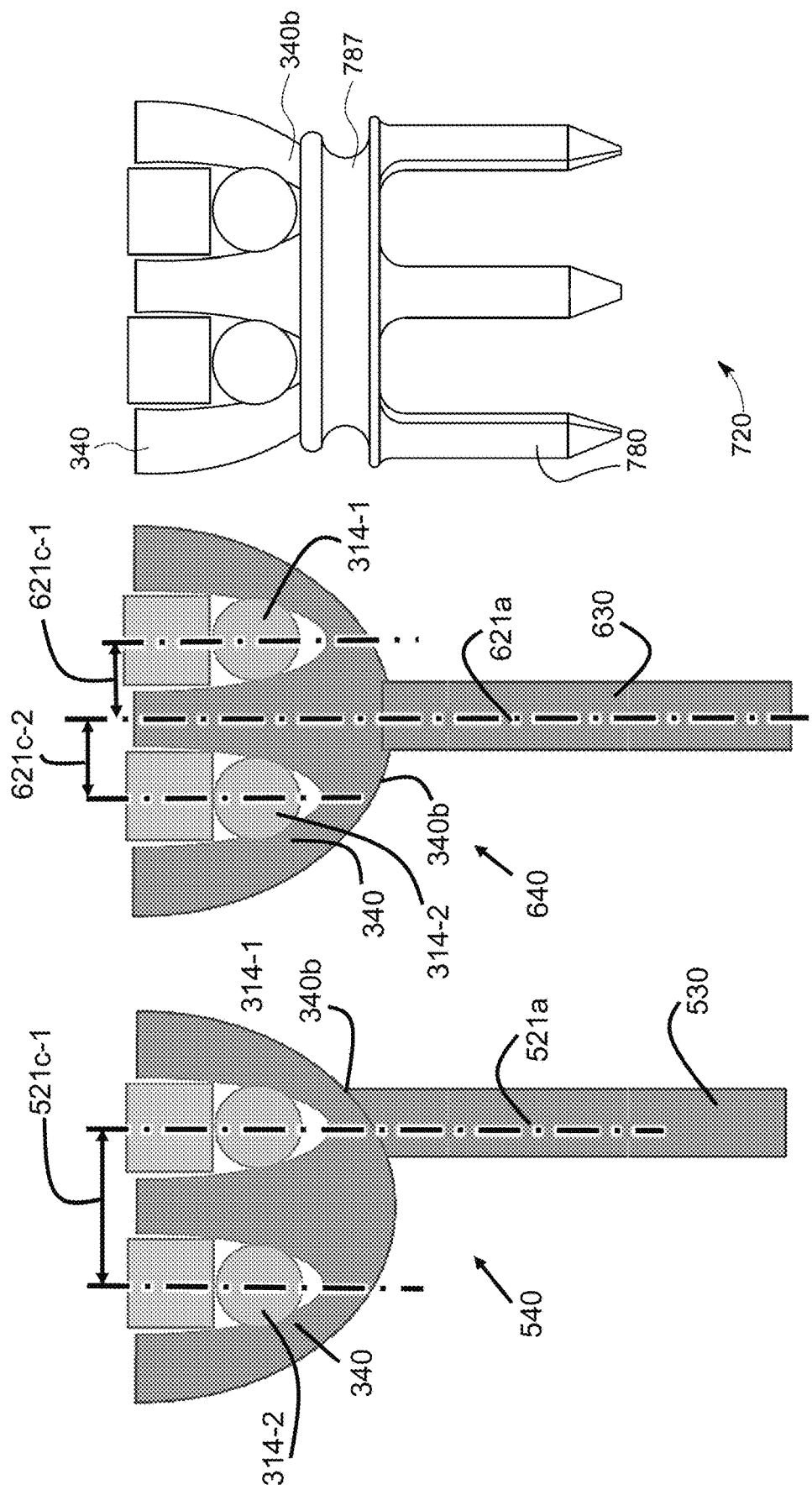

DUAL TETHER SUPPORT OF VERTEBRA

CROSS-REFERENCE TO RELATED APPLICATION(S)

This application claims the benefit of priority to U.S. Provisional Patent Application Ser. No. 62/832,943, filed Apr. 12, 2019, entitled "DUAL TETHER SUPPORT OF VERTEBRA," which is incorporated herein by reference.

FIELD OF THE INVENTION

Various embodiments herein pertain to the field of orthopedics and, more particularly, to apparatuses and methods for coupling one or more bones or bone fragments to each other.

SUMMARY OF THE INVENTION

Some embodiments provide an apparatus for coupling a first bone portion to a second bone portion. The apparatus includes a first flexible connector and a second flexible connector. The apparatus also includes a first bone anchor. The first bone anchor includes a first tethering head. The first tethering head is configured to receive a first portion of the first flexible connector. The apparatus also includes a second bone anchor. The second bone anchor includes a second tethering head. The second tethering head is configured to receive a second portion of the first flexible connector. The apparatus also includes a third bone anchor. The third bone anchor defines a first aperture. The first aperture is configured to receive therethrough the first bone anchor. The third bone anchor also defines a first peripheral channel. The first peripheral channel is configured to receive a first portion of the second flexible connector. The apparatus also includes a fourth bone anchor. The fourth bone anchor defines a second aperture. The second aperture is configured to receive therethrough the second bone anchor. The fourth bone anchor also defines a second peripheral channel. The second peripheral channel is configured to receive a second portion of the second flexible connector.

Some embodiments provide an apparatus for coupling a first bone portion to a second bone portion. The apparatus includes a first member. The first member includes a means for anchoring the first member to the first bone portion. The apparatus also includes a second member. The second member includes a means for anchoring the second member to the second bone portion. The apparatus also includes a means for tensively coupling the first member to the second member. The apparatus also includes a third member. The third member includes a means for anchoring the third member to the first bone portion. The apparatus also includes a fourth member. The fourth member includes a means for anchoring the fourth member to the second bone portion. The apparatus also includes a means for tensively coupling the third member to the fourth member. The apparatus also includes a means for structurally coupling the first member to the third member. The apparatus also includes a means for structurally coupling the second member to the fourth member.

Some embodiments provide an apparatus for coupling a first tether and a second tether to a bone. The apparatus includes a first member. The first member includes a tethering head. The tethering head defines a pathway configured to receive at least a portion of the first tether. The first member includes a means for inserting at least a portion of the first member into the bone. The apparatus also includes a second member. The second member defines an aperture configured to receive therethrough at least a portion of the first member. The second member also defines a peripheral channel configured to receive at least a portion of the second tether. The second member includes a means for inserting at least a portion of the second member into the bone.

Some embodiments provide an apparatus for coupling a first tether and a second tether to a bone. The apparatus includes a tethering head. The tethering head has a pair of first and second opposing arms and a partitioning feature therebetween. The first arm and the partitioning feature define a first pathway configured to receive at least a portion of the first tether. The second arm and the partitioning feature define a second pathway configured to receive at least a portion of the second tether. The apparatus also includes a means for coupling the tethering head to the bone.

Some embodiments provide a method for coupling a first bone portion to a second bone portion. The method includes coupling a first flexible connector that has a first structural characteristic to the first bone portion at a first site. The method also includes coupling the first flexible connector to the second bone portion at a second site. The method also includes coupling a second flexible connector that has a second structural characteristic to the first bone portion at the first site, with the second structural characteristic being different than said first structural characteristic. The method also includes coupling the second flexible connector to the second bone portion at the second site.

It will be appreciated that the various embodiments described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, the figures shown herein may have been created from scaled drawings, scaled models, or from photographs that are scalable. It is understood that such dimensions, or the relative scaling within a figure, are by way of example, and not to be construed as limiting unless so stated in a claim. Persons of ordinary skill will also recognize that CAD renderings may include lines that pertain to changes in surface geometry, and not necessarily to component features.

FIG. 10 is a cross sectional schematic representation of a tethering head according to another embodiment of the present invention.

FIG. 11 is a cross sectional schematic representation of a tethering head according to another embodiment of the present invention.

FIG. 12 is a cross sectional schematic representation of a tethering head according to another embodiment of the present invention.

ELEMENT NUMBERING

Figure 1A:
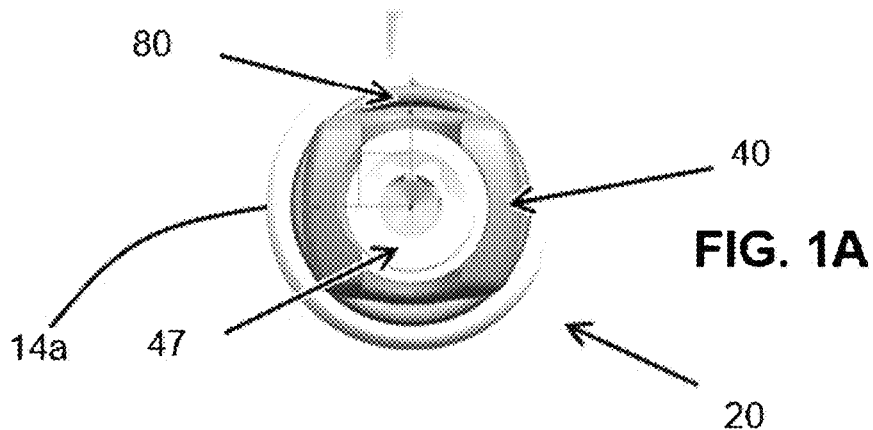
FIG. 1A is a top plan view of a surface rendering of a CAD model of a tethering assembly according to one embodiment of the present invention.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| | |
|---|---|
| 10 | vertebra |
| 11 | bone attachment site |
| 14 | Tether; flexible connector |
| a | loop, bottom |
| b | end |
| c | splice |
| d | top tether |
| 20 | tethering assembly; bone anchor assembly; anchoring device |
| 21a | attachment axis |
| b | radius |
| c | moment arm |
| 24 | set screw |
| a | abutting surface |
| b | bottom surface |
| 30 | fastener; means for attaching a tethering head |
| 31 | staple interface |
| a | threads; locking |
| b | smooth; spherical; rounded |
| c | conical |
| 32 | head |
| 33 | Tip |
| 35 | threads |
| a | double lead cortical threads |
| b | single lead cancellous |
| c | double lead cortical threads |
| 40 | head assembly; means for anchoring a flexible connector; tulip head |
| a | body |
| b | base |

-continued

| | |
|---|---|
| 41 | central aperture |
| 43 | bottom surface |
| 44 | Separator; partitioning feature; divider; barrier |
| c | threads |
| 47 | Flexible connector pathway; tether pathway |
| a | opposing arms |
| b | pathway |
| c | threads, set screw |
| 50 | saddle member |
| 51 | central aperture |
| 57 | arms |
| 57a | top surface |
| 57b | corridor |
| 59 | bottom surface; fastener interface |
| 80 | Staple; plate; strap; means for anchoring a flexible connector; means for attaching a tethering head |
| a | bone facing surface |
| 81 | fastener interface; aperture |
| a | threaded |
| b | smooth; rounded; spherical |
| c | conical |
| 83 | head receiving pocket |
| 84 | projection |
| 86 | groove |
| 87 | tether pathway |
| 88 | eyelet |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that some features 1020.1 and 20.1 may be backward compatible, such that a feature of a later discussed embodiment (NXX.XX) may include features compatible with other various embodiments that were discussed earlier (MXX.XX), as would be understood by those of ordinary skill in the art. This description convention also applies to the use of prime ('), double prime ("), triple prime ('") and star or asterisk (*) suffixed element numbers. Therefore, it is not necessary to describe the features of 20.1, 20.1', 20.1", 20.1" and 20*  that are the same, since these common features are apparent to persons of ordinary skill in the related field of technology.

What follows are paragraphs that express particular embodiments of the present invention. In those paragraphs that follow, some element numbers are prefixed with an "X" indicating that the words pertain to any of the similar features shown in the drawings or described in the text. However, those of ordinary skill in the art will recognize various other non-X prefixed element numbers that discuss features applicable to other embodiments.

This document may use different words to describe the same element number, or to refer to an element number in a specific family of features (NXX.XX). It is understood that such multiple, different words are not intended to provide a redefinition of any language herein. It is understood that such words demonstrate that the particular feature can be considered in various linguistical ways, such ways not necessarily being additive or exclusive.

The use of dual tethers has been suggested as a means of increasing the strength of a vertebral body tethering construct. The concept of dual tethers is explored in the context of the recently developed "segmental pedicle screw style anchor." However, this idea could be applied for any tethering anchor/screw/staple combination capable of accepting two distinct lengths of tether material. An example of a dual tether construct is shown in FIGS. 5, 6, 7, and 16.

Figure 6:
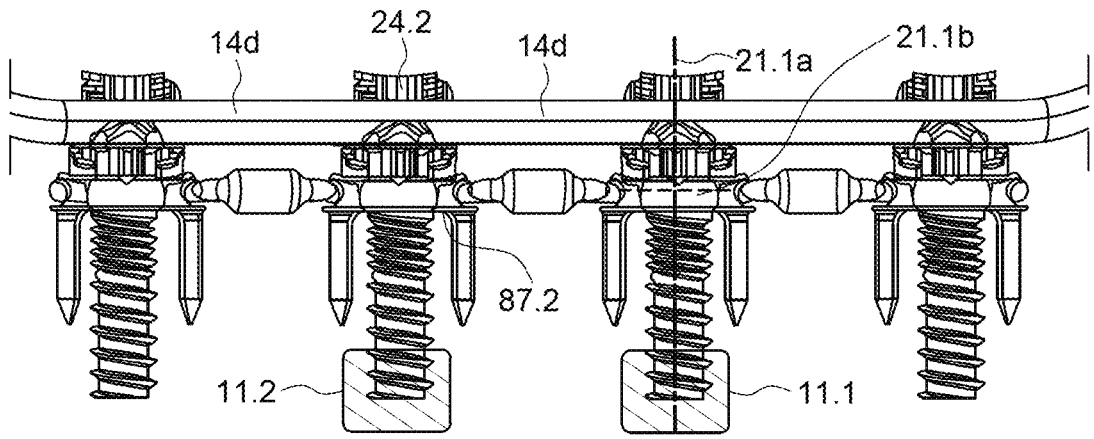
FIG. 6 is a side elevational, cross sectional representation of the interconnected plurality of devices of FIG. 5.

In the dual anchor construct shown in FIG. 6, one example of a tether cord (~4 mm diameter polymer braided cord) is shown locked between the tulip heads X40 of each anchor via compression of the set screws X24 (flexible connector X14d). In this specific design, flexible connector X14a is a less traditional tether design. Here, flexible connector X14a is a continuous piece of material, but the cord is bifurcated and/or spliced at regular intervals to form circular loops. Each loop fits around the grooves in each of the staples X80. If the cord is simply bifurcated, the loops will occur at regular/fixed intervals, using a pre-determined spacing of the staples. If the cord is spliced in multiple spots to create the loops, the loops could be simultaneously or sequentially cinched tight to adjust the spacing between the staples. Other anchor designs may allow a more traditional cord to be used for flexible connector X14a in which case there would simply be two lengths of round cord running between the anchors.

Dual tethers, in the following configurations, may be used for one or more of the following benefits.

Two flexible, axially stiff tethers (e.g. braided polymer cord/rope) may be used to increase the strength and stiffness of a tethered construct. Axial strength and stiffness are increased without increasing the overall profile/height of the anchors X20 because the tether material can be distributed across two different attachment points. For example, two 4 mm cords may be attached in two different spots, rather than just running a single 6 mm cord between the tulip heads (the latter of which would benefit from higher tulip head profile/height). Axial strength and stiffness can be increased with a lower increase in bending stiffness of the tethers. For example, two separate 4 mm cords may have a lower bending stiffness than a single 6 mm diameter cord. Maintaining flexibility in bending is useful for a vertebral body tethering procedure. Dual tethers can provide redundancy in case one tether is damaged/fractures.

Two tethers of varying stiffness could be employed so that the second tether (flexible connector X14a) begins supporting load once the first tether (flexible connector X14d) is stretched to a certain predetermined point. This configuration could be used to allow some stretch in the primary tether, while preventing overload failure of the primary tether. A similar effect could be achieved by tensioning flexible connector X14d and flexible connector X14a to different initial tension levels.

Flexible connector X14d could be made of a rather stiff, substantially inelastic polymer cord, for example, while flexible connector X14a could be made from a substantially elastic material (or vice versa). As used herein, "substantially elastic" (and inflections thereof) means that the thing referred to is capable of an elastic longitudinal deformation of at least about a millimeter when typical physiological loads are applied; while "substantially inelastic" means that the thing referred to is not substantially elastic. In some embodiments, flexible connector X14a could be capable of an elastic longitudinal deformation of up to about 5 millimeters under typical physiological loads, while flexible connector X14d could only be capable of an elastic longitudinal deformation of less than 1 millimeter (perhaps only fractions of a millimeter) under typical physiological loads (or vice versa). It should be appreciated that in some such embodiments flexible connector X14a could have a substantial elasticity comparable to that of a typical intervertebral disc, while in such embodiments flexible connector X14d could be much stiffer (or vice versa). It should also be appreciated, then, that for intervertebral coupling of a curved spine, some embodiments could allow for noticeable lengthening of the concave side of the spine when the patient bends. In a similar vein, in some embodiments flexible connector X14d could have a tensile elasticity that is significantly less than that of flexible connector X14d (or vice versa). In some such embodiments, the modulus of elasticity of flexible connector X14d could be less than about 25% of the modulus of elasticity of flexible connector X14d (or vice versa). In some scenarios, flexible connector X14a could provide continuous compressive load to the vertebrae (prohibiting growth) even when flexible connector X14d is offloaded as the patient flexes in certain ways. As the patient flexes the opposite way, flexible connector X14a could act as a shock absorber, providing a gradual ramp-up of tensile load until flexible connector X14d sharply and stiffly restricts motion. Alternatively, flexible connector X14d could be locked in place so that it has some initial slack. Elastic flexible connector X14a would provide most of the growth modulation and flexible connector X14d would only kick in under extreme loading events.

Dual tethers could provide a way to stage growth modulation. In one example, flexible connector X14d could be tensioned tightly, and flexible connector X14a could be left slack during the implantation procedure. The diameter/strength of flexible connector X14d could be chosen so that it fractures after a given amount of patient growth/time. At that point flexible connector X14a could kick in to provide additional growth modulation. In this situation, growth modulation could be "reset" from a different starting point. Also, because flexible connector X14a was left slack and did not see load during initial cycling, it would be starting fresh from a fatigue-life point of view. This could increase the fatigue life of the tethered construct. As an alternative, flexible connector X14a could be left extra-slack, so it just supports the spine without significant growth modulation after flexible connector X14d fractures. Accordingly, in some embodiments flexible connector X14d and flexible connector X14a could each have a respective tensile strength, with the tensile strength of flexible connector X14d being less than or equal to 50% (or otherwise significantly less) than the tensile strength of flexible connector X14a (or vice versa). In some such embodiments, the tensile strength of flexible connector X14d could be about 1500 newtons or less with the tensile strength of flexible connector X14a being about 3000 newtons (or vice versa). In some embodiments flexible connector X14d and flexible connector X14a could each have a respective uniform cross-sectional area, with one of the cross-sectional areas being significantly less than the other. In some such embodiments, the uniform cross-sectional area of flexible connector X14d could be more than 25% less than the uniform cross-sectional area of flexible connector X14a (or vice versa). In some embodiments flexible connector X14d could have an initial tension of about 100-300 newtons (or otherwise significantly greater than zero, where, as used in this context, "significantly greater than zero" means a force suitable to produce a clinically significant realignment of one or more vertebrae) and flexible connector X14a could have an initial tension of about 25 newtons or less (or otherwise practically zero, where, as used in this context, "practically zero" means around just enough force to take up any slack without producing a clinically significant realignment of any vertebrae) (or vice versa). Alternatively, flexible connector X14d could be intentionally severed during a minimally invasive revision procedure, allowing flexible connector X14a to either continue growth modulation or support the spine as described above. A revision procedure to cut the cord would be less involved than a procedure to completely replace a cord. In another example, flexible connector X14a could be tensioned tightly, and flexible connector X14d could be left slack. Both scenarios described above could be implemented to mitigate the risk of overcorrection of the spine, which can occur if a tether is too tight and/or left in place too long.

Figure 5:
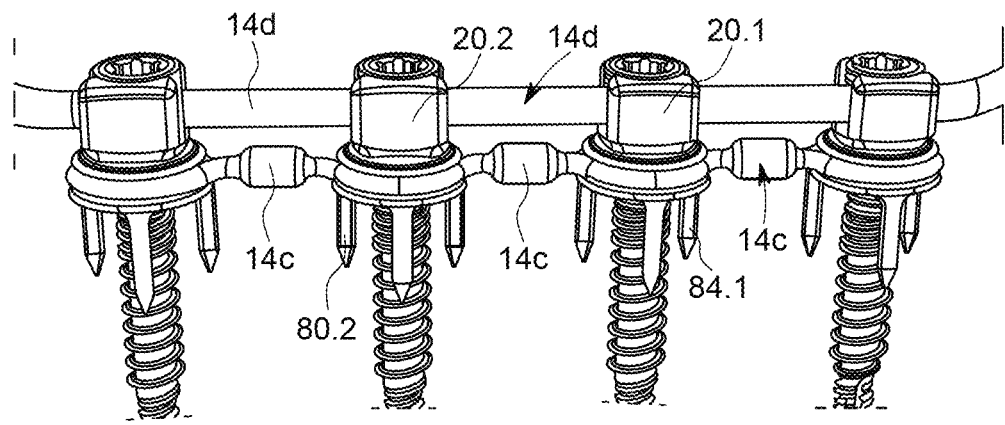
FIG. 5 is a perspective representation of an interconnected plurality of the apparatus of FIG. 1A.
Figure 7:
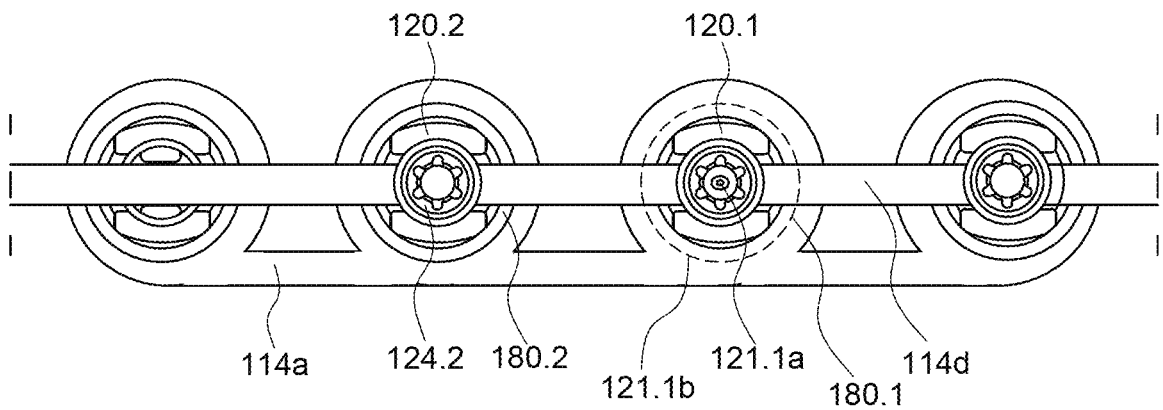
FIG. 7 is a top true perspective top view of the apparatus of FIG. 6.

Dual tethers could provide a means of providing growth modulation in a second plane. As shown in FIGS. 5, 6, and 7, the two tethers extend in alignment with the attachment centerlines X21a of the anchors. In some embodiments, the anchors X20 are placed along the centerline of the vertebrae, although in various other embodiments of the invention the anchors X20 can be placed anywhere on the vertebrae, or anywhere on other bones of the body, and also between a bone and a fragment of bone. Tension in each of the cords provides tension along the same vector and rotational moments in the same plane so the spine corrects in at least a single plane. Another embodiment of the dual tethers concept places one or more of the tethers off the centerline of the anchors, with one example shown in FIG. 7. This is done by changing the construction of the individual loops on the cord: the loops wrap around the staples, like before, but now the loops are connected along a tangent to a radius X21b of attachment axis X21a rather than along their attachment axes X21a. Any application of tension along the offset tether can induce a bending moment in a second plane. If the primary tether (flexible connector X14d) is meant to correct scoliosis, the secondary tether (flexible connector X14a) will induce kyphosis or lordosis depending on the relative positioning of the flexible connectors.

Figure 8:
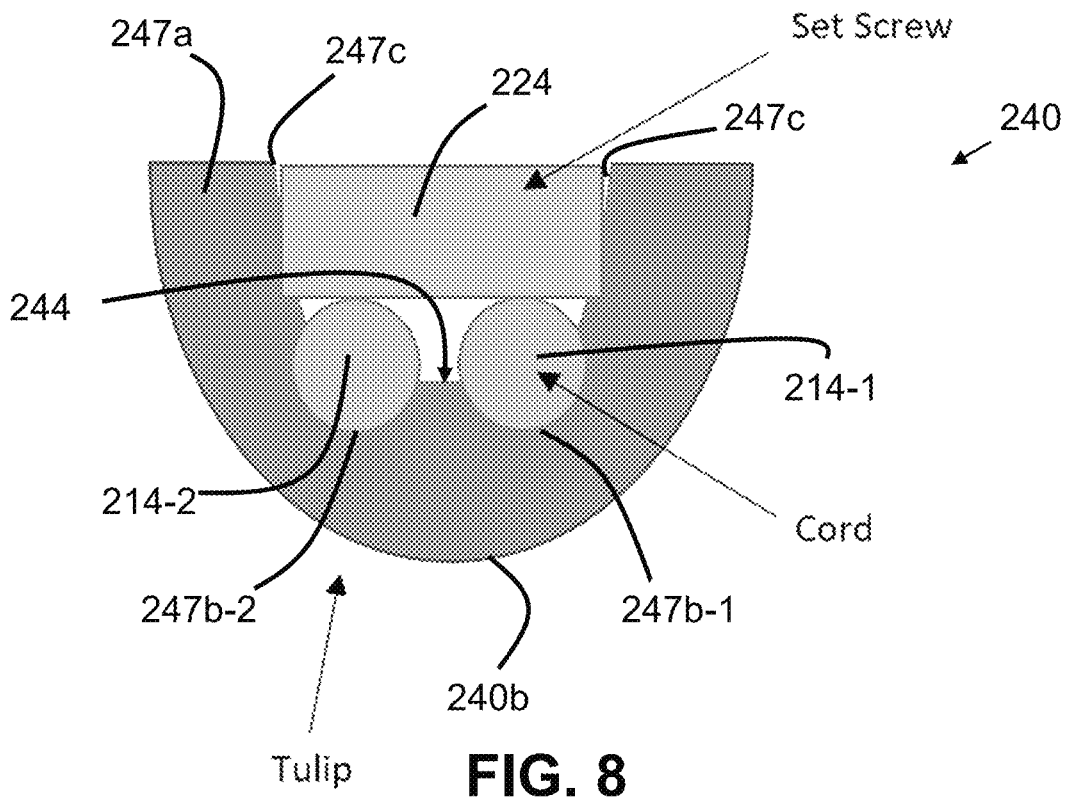
FIG. 8 is a cross sectional schematic representation of a tethering head according to another embodiment of the present invention.

Yet another manner of accomplishing the offset situation achieved by the tangential loading discussed above is expressed in an embodiment that changes the design of the anchor so that the tulip head X40 can accept two, side-by-side lengths of cord. Exemplary cross sections are shown in FIGS. 8, 9, 10, 11, and 12. The tulip head could be configured so that there is a single, partially divided opening that accepts two lengths of tether, with a single set screw that locks both lengths of tether in place as shown in FIG. 8. Or, the tulip head could have two distinct cutouts, each accepting a single length of tether with individual set screws that lock each cord in place, as shown in FIGS. 9, 10, 11, and 12. Moving one of the axes of the cords off center from the axis of the screw shank induces a moment that could induce kyphosis or lordosis, as shown in FIG. 10.

Figure 1B:
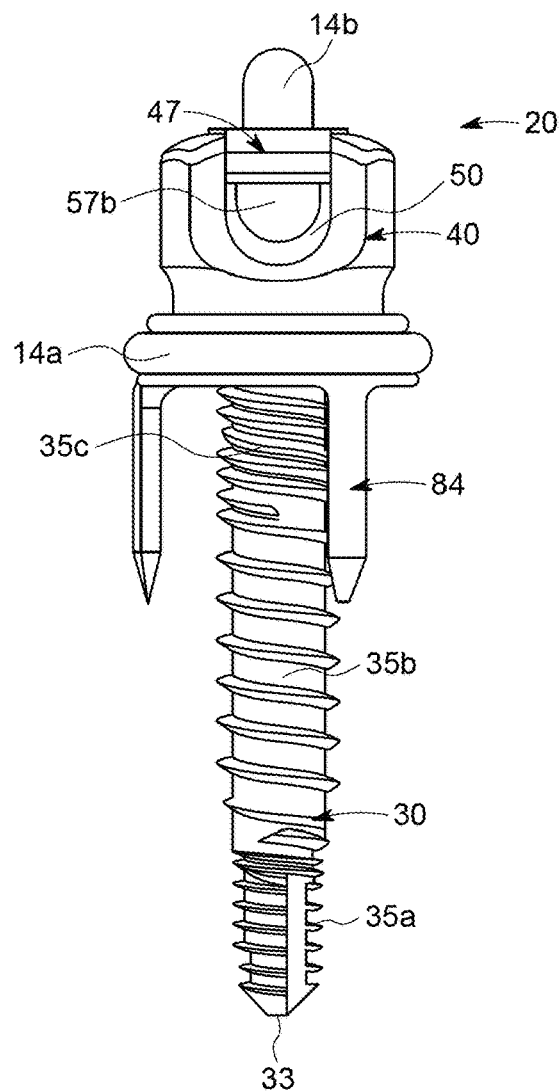
FIG. 1B is a front elevational view of the apparatus of FIG. 1A.
Figure 2:
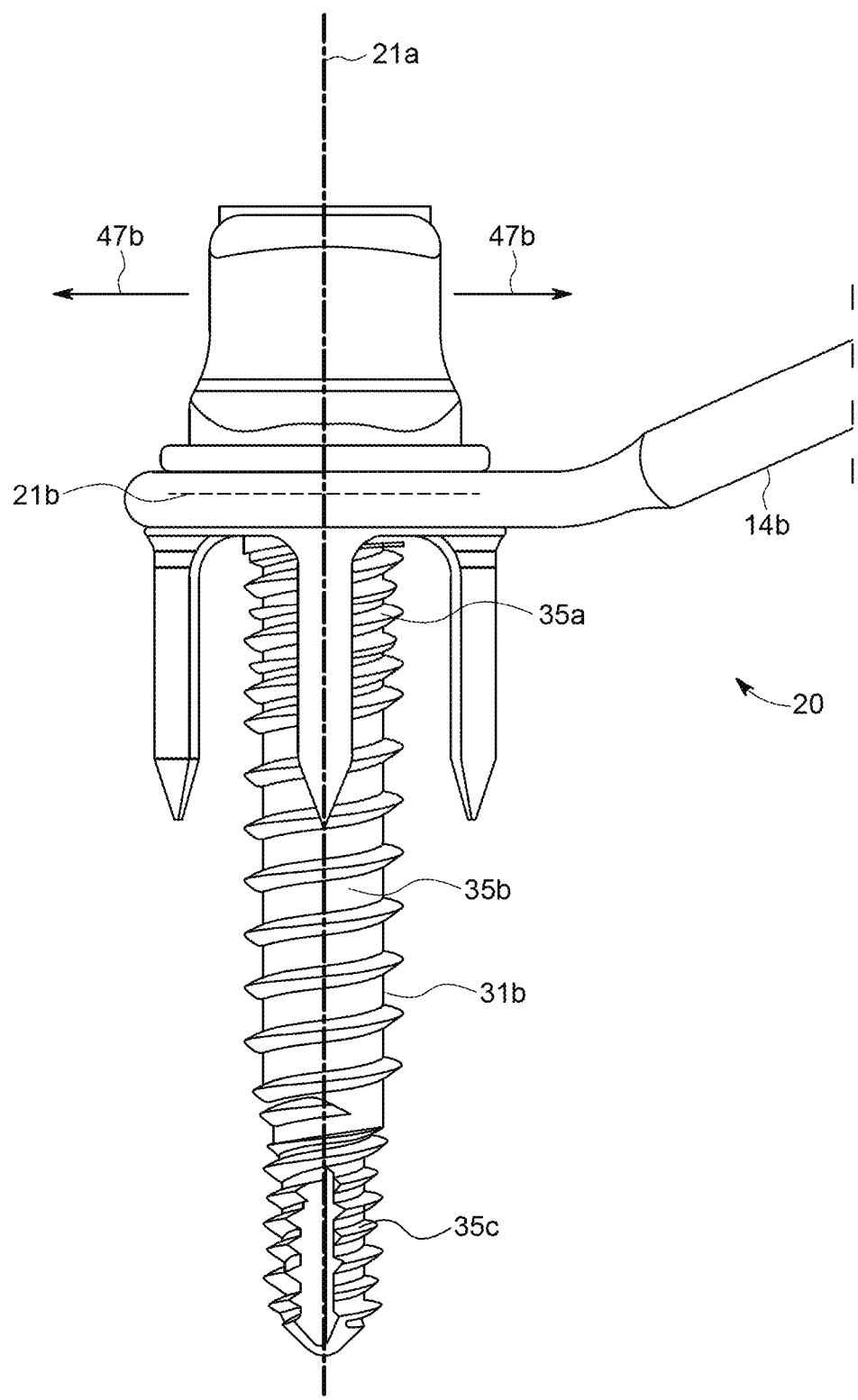
FIG. 2 is a side elevational view of the apparatus of FIG. 1B.

Referring to FIGS. 1A and 1B, it can be seen that the combined tethering assembly 20 includes a head assembly 40 including a set screw 24, internally received saddle member 50 and collar member 60. This head assembly 40 is rotatably captured after assembly to the head 32 of a bone fastener 30, although it will be seen that in still other embodiments the head assembly X40 may be integral with a bone fastener X30. After implantation, the bone fastener is securely received within an aperture and fastener interface 81 of a staple 80. The implanted device X20 is coupled to a vertebra (or other bone, in non-spinal applications) by both the threads X35 of fastener X30, and by the projections X84 of staple X80. In one embodiment, a fastener X30 includes larger double lead cortical threads 35a proximate to the point of entry of the fastener into the vertebra, a midsection with single lead cancellous threads 35b, and near the tip 33 a section of smaller double lead cortical threads 35c for connection to the distal side of the vertebra. However, it is understood that various embodiments of the present invention contemplate any manner of attaching a head X40 to a vertebra, whether by a fastener or by other means, and including fasteners having only cortical and cancellous thread, or only cortical thread. In some embodiments the head X40 may also be attached to the vertebra or bone by devices including straps.

In one embodiment, the head assembly X40 is rotatably coupled to, and captures, head X32 of fastener X30. Further discussion of various head assemblies X40 useful in the embodiments disclosed herein can be found in U.S. provisional patent application Ser. No. 62/811,318, titled TETHERING PEDICLE FASTENER, filed Feb. 27, 2019, which is incorporated herein by reference. In one embodiment, head assembly X40 is generally free to rotate about the centerline 21. An embodiment permitting polyaxial movement of the spherical head of the fastener X30 relative to a tethering head X40 is further described within the above-referenced provisional patent application.

Referring to FIGS. 3, 4, 13, and 14, some embodiments include a staple X80 adapted and configured for fixation to a bone. Although anchoring member X80 can be coupled to the bone in any manner, the coupling of members 80, 180, 480, 580, and 780 to the bone is by way of a plurality of projections 84 that are adapted and configured to penetrate the cortical layer of bone. However, it is also understood that means for anchoring a flexible connector X80 can include a plate, strap, or other means for connecting an anchor to a bone.

Figures 3, 4:
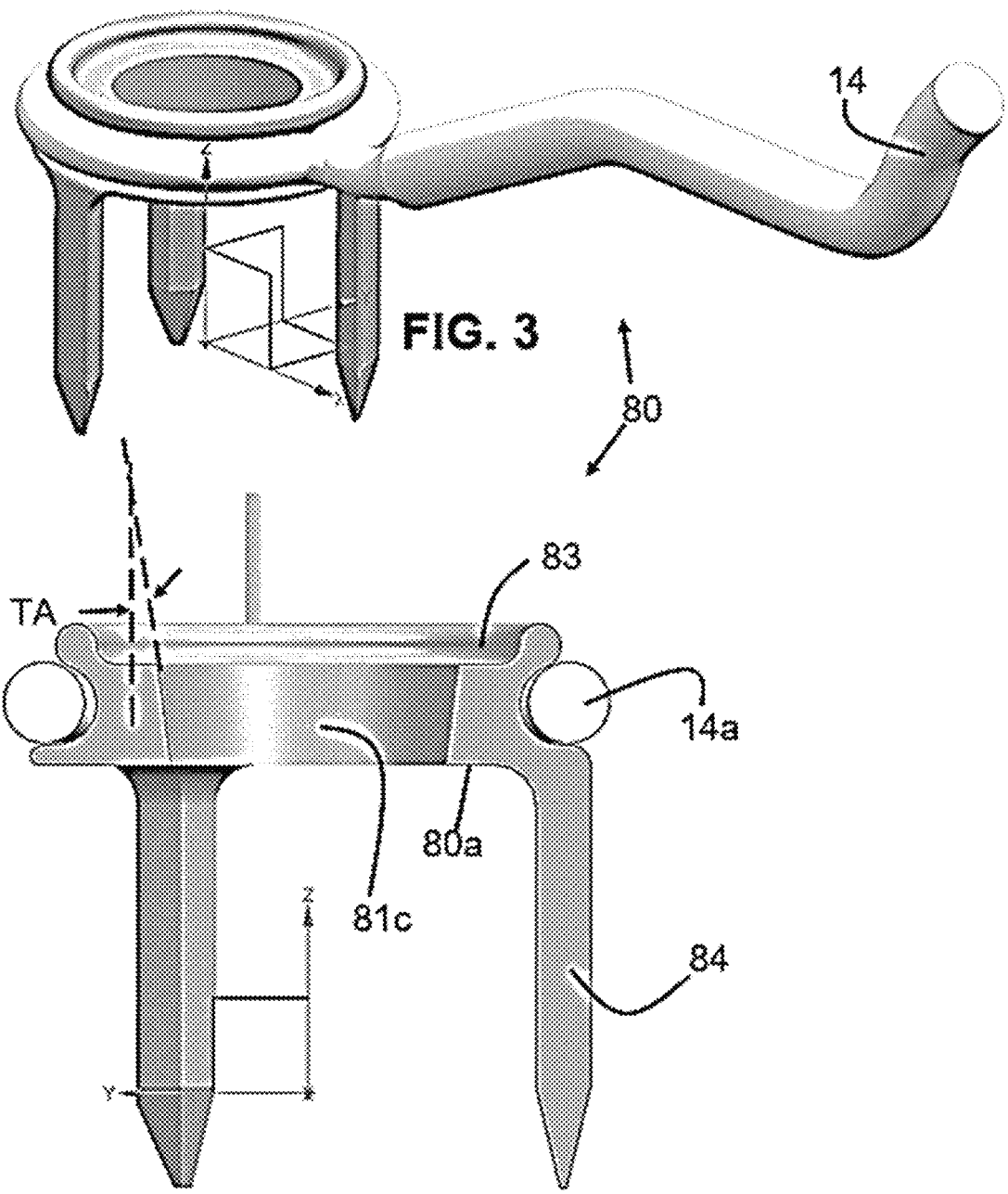
FIG. 3 is a side, top perspective view of a portion of the apparatus of FIG. 1A.
FIG. 4 is a side elevational, cross sectional view of the apparatus of FIG. 3.

As best seen in FIGS. 3 and 4, a member 80 preferably includes a plurality of projections 84 that are circumferentially spaced around the periphery of member 80. Further, member 80 preferably includes a circumferential groove 86 that is sized to receive within it a loop 14*a* of a flexible material. In some embodiments, this loop is fabricated around staple 80 during manufacturing, such that a device 20 is available to the user with a pre-attachment of a section of flexible connector 14, having both the loop 14*a* and a free end 14*b* (as best seen in FIG. 6). Yet other embodiments contemplate the looping of a flexible connector onto a member 80 at any time prior to or during implantation, and in still other embodiments a member X80 that is not looped or otherwise connected to a flexible connector.

In yet other embodiments of the present invention, the anchoring device X20 comprises a head assembly X40 that is attached to a bone in any manner, including as examples bodies X40*a* that include integral projections, cortical threads, interfaces for strap-type attachments, and the like. In such embodiments, there need not be a separate fastener. In still further embodiments, the anchoring device comprises a head assembly X40 and a fastener X30, but without any staple member X80.

In this manner, and referring again to FIGS. 1B and 5, it can be seen that in some embodiments this hard abutting contact between the set screw and an internal saddle 50 establishes a region in the corridor 57*b* that has a fixed cross sectional area. In some embodiments, this cross sectional area is approximately D-shaped, although yet other embodiments contemplate any manner of shape created by the abutment of the set screw and at least one of the arms 57. In some embodiments, this cross sectional area is selected to provide a predetermined amount of compression onto a flexible member placed within the corridor. In still further embodiments, the set screw is tightened to frictionally restrain the tether within the corridor, but without any abutting contact between the set screw and the saddle member.

In those embodiments utilizing certain tethering materials fabricated from organic polymers, the predetermined, fixed cross sectional area of the corridor can be less than about fifty percent of the free, uncompressed cross sectional area of the tether, and in still further embodiments less than about thirty percent of the free, uncompressed tether cross sectional area. Those of ordinary skill in the art will recognize that the selection of the geometric features for the fixed cross sectional area of the corridor of the fully assembled head 40 can be selected based on the type of material used for the flexible material (noting for example differences between a wound metallic material and a polymer), as well as for differences in the method of manufacturing (comparing for example loosely packed polymer material vs. densely packed polymer material).

FIGS. 8-12 show various embodiments of anchoring means X40 that are adapted and configured to constrain a plurality of flexible connectors X14. Referring to FIG. 8, an anchoring means 240 is shown schematically. A pair of opposing arms 247*a* extend upward from a base 240*b*. The inner, opposing faces 247*c* of arms 247*a* are threaded so as to couple to a set screw 224. A partition or divider 244 extends upward toward the bottom of the set screw, and is located on the inside of the bottom of the base 240*b*. This central divider 224 and the opposing arms define a pair of flexible connector pathways 247*b*-1 and 247*b*-2. Each of these pathways is adapted and configured to receive within it a flexible connector 214-2 or 214-1, respectively. The flexible connectors are locked into a position relative to base 240*b* by compression against the underside 224*b* of the set screw 224. Anchoring means 240 can be attached to an attachment site on a bone by any of the methods and apparatus discussed herein, including any of the anchoring means X80.

Figure 9:
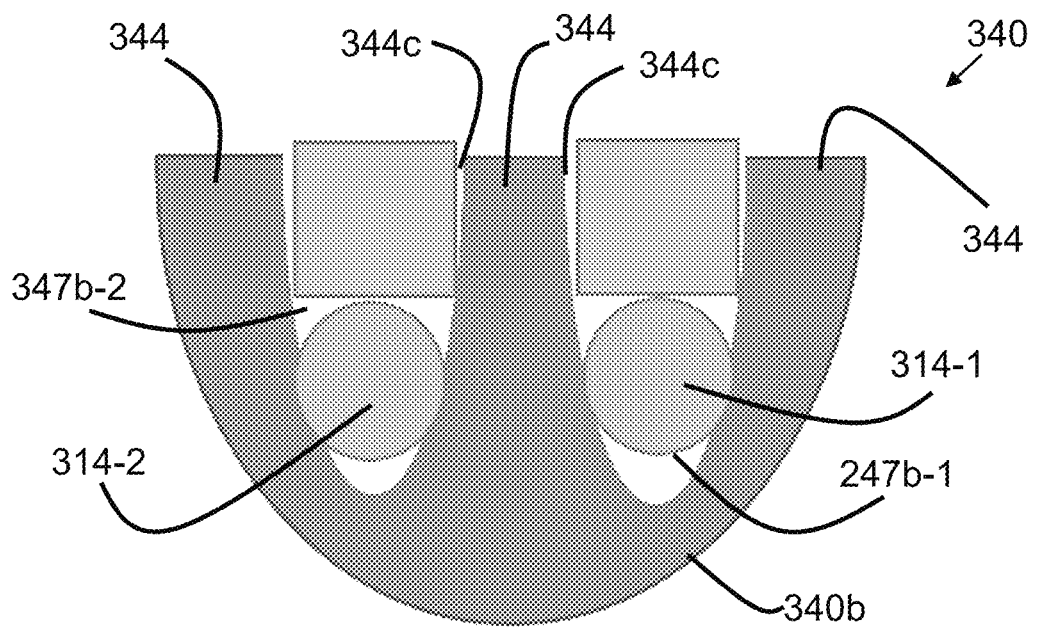
FIG. 9 is a cross sectional schematic representation of a tethering head according to another embodiment of the present invention.
Figure 13:
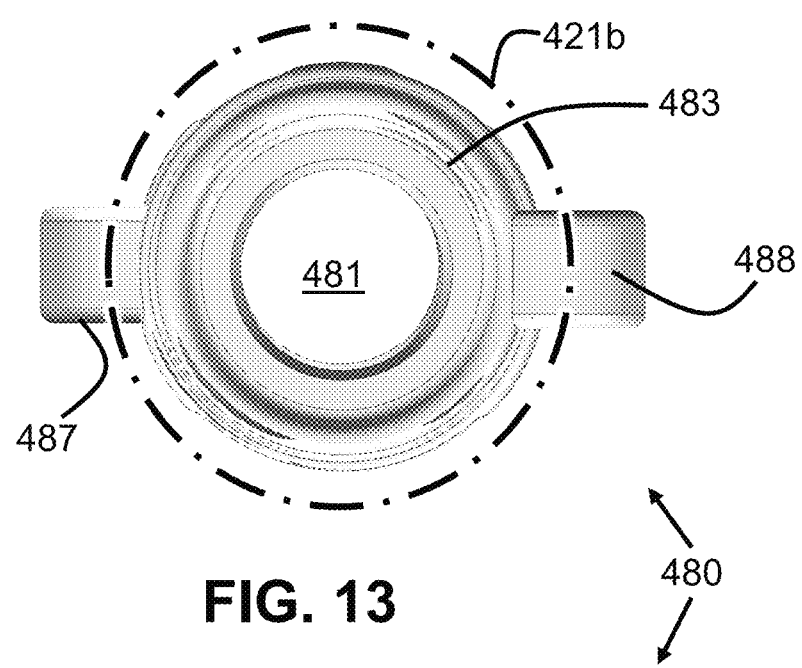
FIG. 13 is a top plan view of a device useful for anchoring together two adjacent bones or bone fragments according to another embodiment of the present invention.
Figure 14:
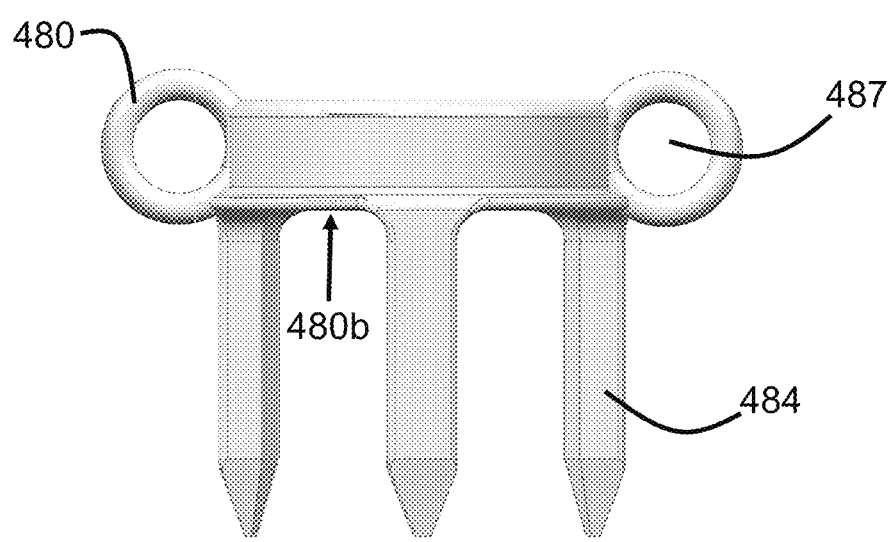
FIG. 14 is a side elevational view of the apparatus of FIG. 13.

Referring to FIG. 9, an anchoring means 340 is shown schematically. A pair of opposing arms 347*a* extend upward from a base 340*b*. The inner, opposing faces of 347*c* are threaded so as to couple to a set screw 324. A partition or divider 344 extends upwardly to a height about the same as that of the arms 347*a* on either side of the partition, and is located on the inside of the bottom of the base 340*b*. The partition 344 includes threaded surfaces 344*c* that are each adapted and configured to couple with a corresponding, opposing threaded surface 347*c*, such that the flexible connector within each pathway 347*b* is frictionally locked by its own set screw. This central divider 344 and the opposing arms define a pair of flexible connector pathways 347*b*-1 and 347*b*-2. Each of these pathways is adapted and configured to receive within it a flexible connector 314-2 or 314-1, respectively. The flexible connectors are locked into a position relative to base 340*b* by compression against the underside 324*b* of individual set screws 324. Anchoring means 340 can be attached to an attachment site on a bone by any of the methods and apparatus discussed herein, including any of the anchoring means X80.

FIGS. 10, 11, and 12 depict embodiments in which anchoring means X40 can be coupled to an attachment site of a bone. Although these three figures each use anchoring means 340, it is understood that this is by way of example only, and any of the anchoring means X40 can be attached to a bone by any of the apparatus or methods discussed herein.

Referring to FIG. 10, it can be seen that as one example a fastener 530 (shown schematically) can be attached to head 340 so as to be in general vertical alignment with one of the tethers. Fastener 530 establishes a spatial separation of tether 314-2 from attachment axis 521*a* by a moment arm 521*c*-1. Persons of ordinary skill in the art will understand that a tensile force applied to flexible connector 314-2 will create a moment about attachment axis 521*a*, and likewise apply that moment to the attachment site 11.

FIG. 11 schematically depicts an anchoring means 640 in which the fastener 630 establishes an attachment axis 621*a* between the flexible connectors 314-2 and 314-1. A tensile force attached to connector 314-2 will establish a moment about attachment axis 621*a* by the action of that tensile force operating at a distance 621*c*-2 from the central axis. Likewise, a tensile force applied to flexible connector 314-1 will establish a moment in the opposite direction about attachment axis 621*a* based on action at a spatial displacement represented by the arrow 621*c*-1. In some embodiments of the present invention, the two offset distances 621*c*-2 and 621*c*-1 are generally the same, although in yet other embodiments the two distances can be any length, such that the net moment applied to the attachment site is the combination of these two individual moments.

FIG. 12 is a schematic representation of an anchoring assembly 720 that includes a first anchoring means 340 coupled to a second anchoring means 780. In some embodiments, tethering assembly 720 provides the surgeon with an opportunity to interconnect the two bone attachment sites by a third flexible connector within pathway 787 (or in still further alternate embodiments, through eyelets 788 (not shown)).

FIGS. 13-16 show various embodiments of an anchoring device 420 according to another embodiment of the present invention. Anchoring device 420 is similar to that of embodiments 20, 120, or 320, except that staple 480 includes a plurality of eyelets 488 that preferably extends radially outwardly from multiple sides of outer surface 486.1. Preferably, eyelet 488 defines a central aperture that provides a tether pathway 487. Referring to FIGS. 36 and 37, it can be seen that eyelets 488 each include a central aperture 481 that defines tether pathways 487. However, it is understood that the eyelet can be oriented in any manner from the outer surface of the staple, and further the tether pathway can have any angular orientation relative to the central aperture of the staple. It is understood that the interface between the staple and the fastener can be of any type described herein. Although what has been shown and described pertains to means for anchoring 480 that includes a pair of eyelets located on opposite sides of the circumference, it is understood that yet other embodiments of the present invention contemplate any orientation of the eyelets around the circumference, and further include those embodiments having a single eyelet.

Figure 15:
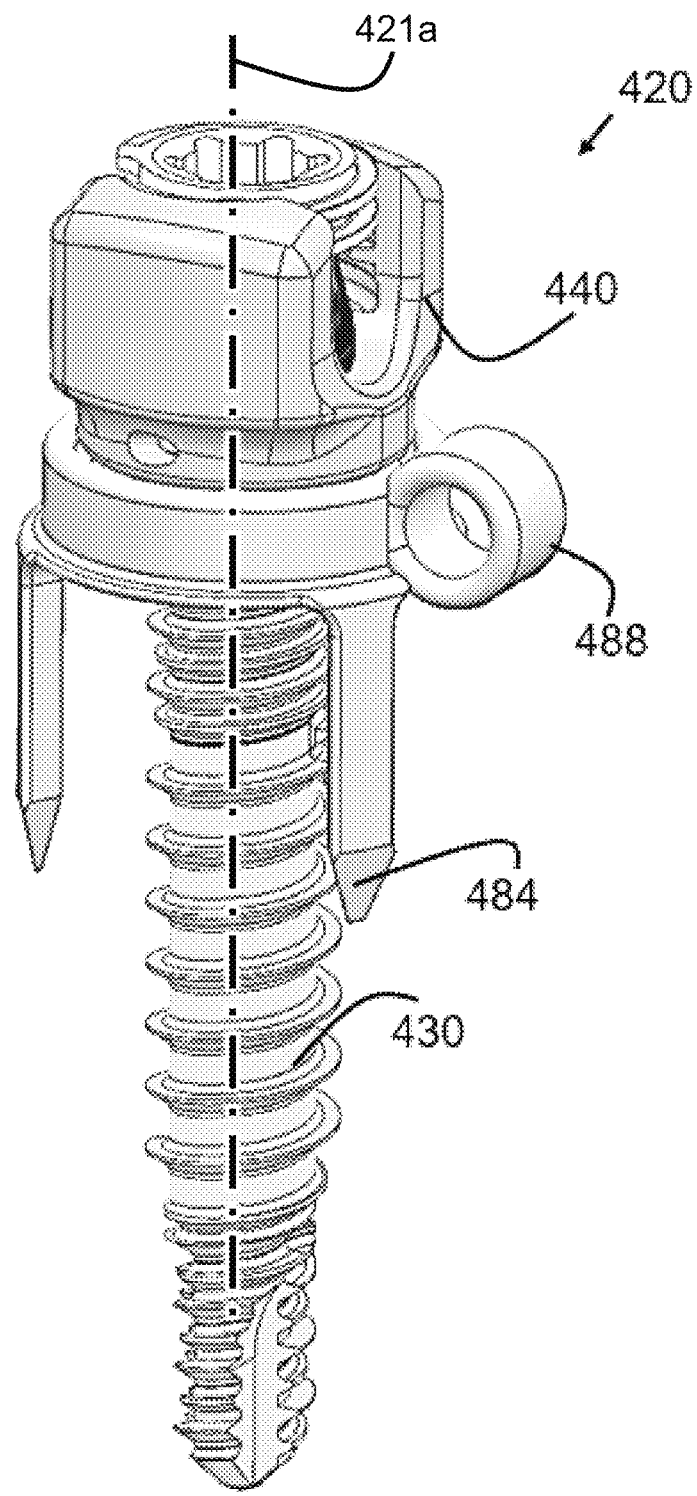
FIG. 15 shows a portion of the apparatus of FIG. 13 coupled to another means for anchoring a flexible connector.

FIG. 15 shows an assembly 420 including a means for anchoring 480 that is coupled to a means for anchoring 440. As shown, the assembly 420 is adapted and configured to be attached to a single site 11 of a bone, with attachment axis 421a establishing a location of the site, and with the centerlines of the eyelets 488 establishing a radius of attachment generally centered about attachment axis 421a. For simplicity, FIG. 15 shows a single eyelet 488, but it is understood that multiple eyelets, circumferentially arranged, are contemplated. Although what has been shown and described herein is a radius of attachment X21b that is centered about an attachment axis, it is understood that other embodiments of the present invention contemplate circular attachment shapes that are not centered about the attachment axis X21a, and further those embodiments in which a noncircular locus of attachment points for tangential loading (oblong, elliptical, rounded shapes, or the like) is contemplated. In such asymmetrical embodiments, the surgeon is presented with mounting options that provide for a range of different length moment arms useful in providing different levels of torque to the bone attachment site from a single configuration of anchoring means X80.

Figure 16:
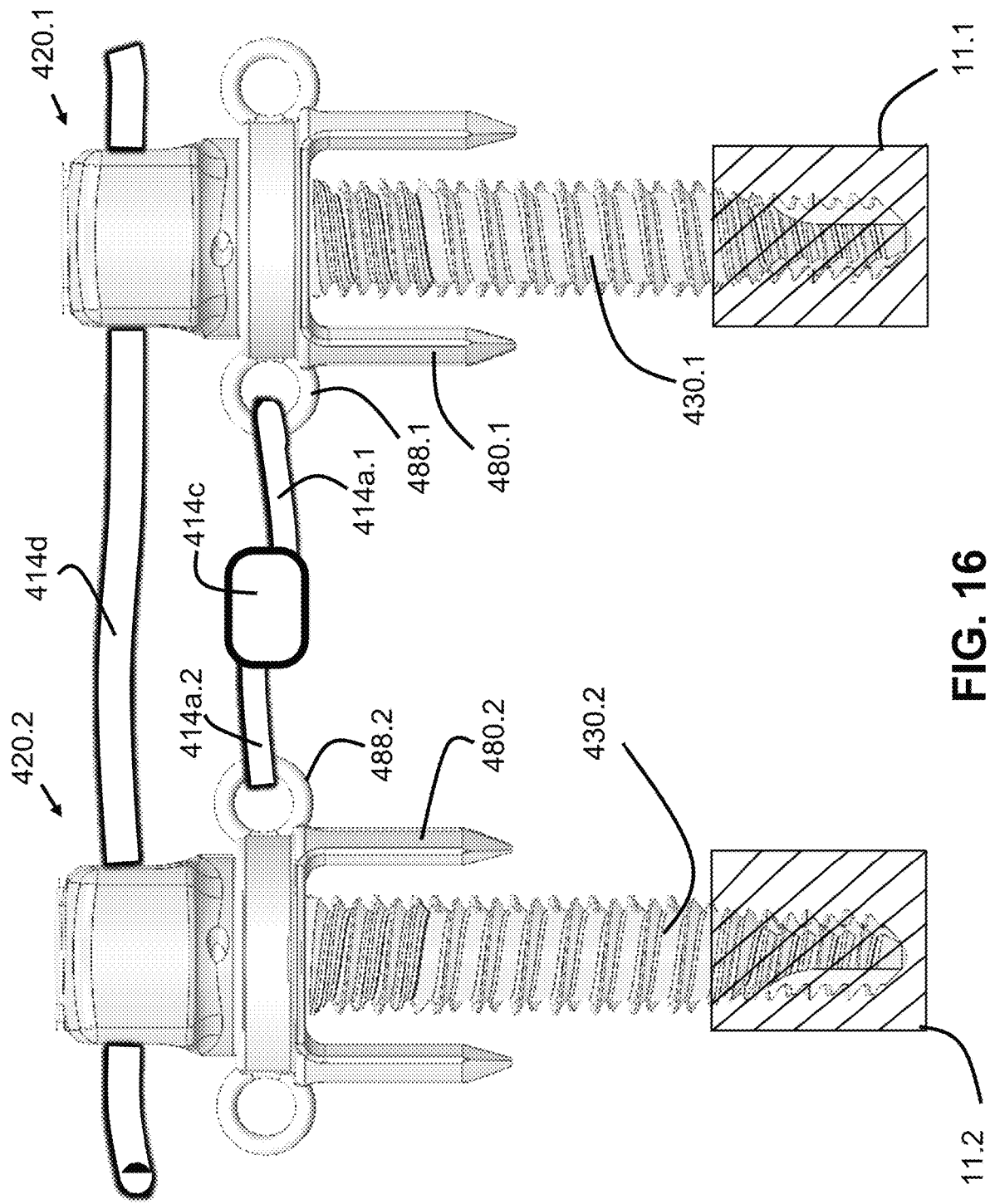
FIG. 16 shows a pair of devices of FIG. 15 interconnected to one another.

FIG. 16 shows a pair of devices 420.1 and 420.2 that are adjacent to one another. In one embodiment, a loop 414a.1 extends from eyelet 488.1 and through aperture 487.1. A second loop 414a.2 extends from eyelet 488.2. The free ends of the two portions of bottom tether are coupled together in a central splice 414c. In the embodiment shown, the anchoring means 480.2 and 480.1 are arranged such that the adjacent most eyelets 488.2 and 488.1 are directly opposite one another, so as to provide tension in the spliced bottom tether. Further, the bottom tether is shown in general alignment with the top tether 418d. However, it is understood that either of the anchoring means 480.2 or 480.1 could be rotated, such that tension in the spliced bottom flexible connector applies a moment of bone attachment site 11.1 relative to bone attachment site 11.2.

The configuration of FIG. 16 further shows a top flexible connector 414d. This top flexible connector 414d extends through a corridor 457b.2 of adjacent anchoring device 420.2, and is frictionally captured within head 440.2. Top flexible connector 414d further extends through the corridor 457b.1 of adjacent anchoring device 420.1, and is also captured within head 440.1. The free ends 414b.1 of tether 414d extend loosely out from heads 440.2 and 440.1. It is understood that these free ends can couple to still further tethering assemblies X20 (not shown), or may simply terminate as loose ends.

Figure 17:
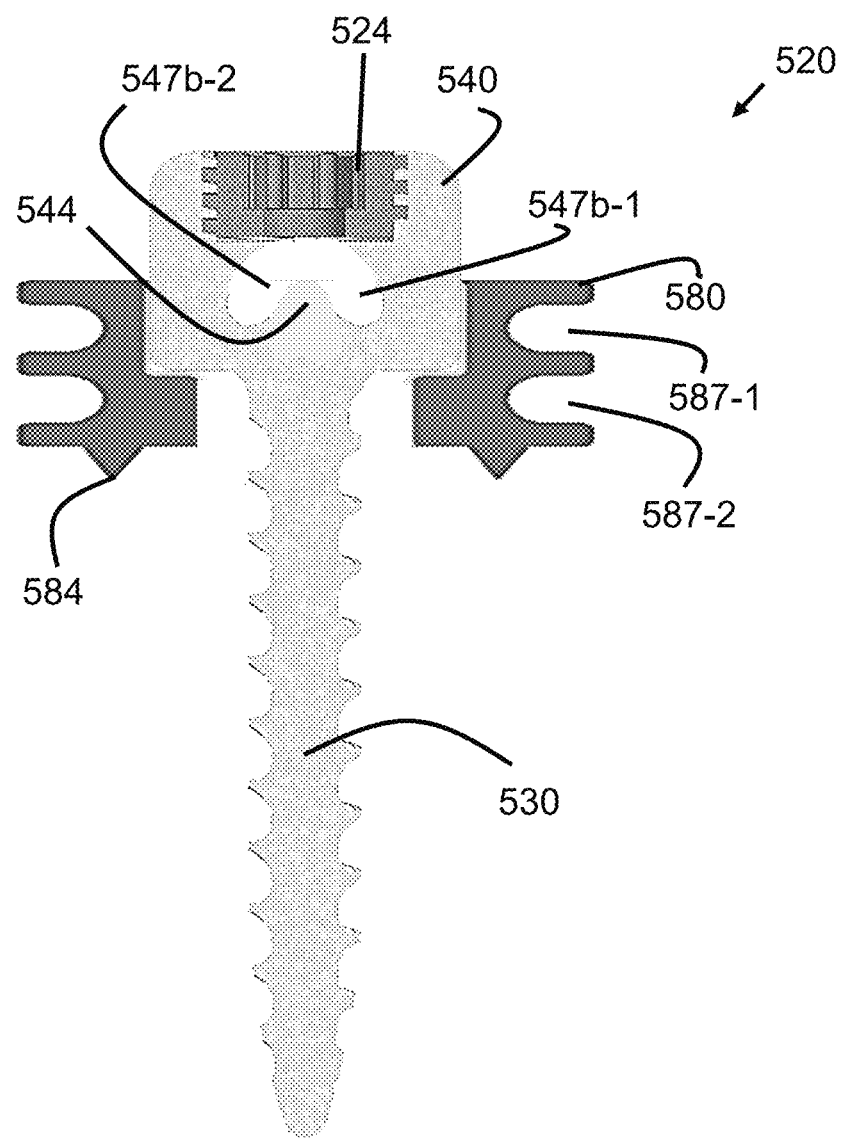
FIG. 17 is a side elevational, cross sectional representation of an apparatus according to yet another embodiment of the present invention.

FIG. 17 shows yet another embodiment of a tethering assembly 520. Bone anchoring assembly 520 includes an anchoring means 540 that is attached to an integral width a bone fastener 530. Head 540 includes within it a pair of internal pathways 547b-2 and 547b-1 that are established by opposing arms 547a, and barrier 544 placed centrally in the interior of the head. A set screw 524 can be used to apply compression against the flexible connectors (not shown) so as to lock their positions relative to head 540. A second anchoring means 580 is shown receiving within a central aperture the anchoring means 540. Staple 580 includes a pair of generally parallel tether pathways 587-1 and 587-2.

Various embodiments are also described at least in part in the following statements:

A. An apparatus for attaching two bones to one another, comprising: a first bone anchor having a first tethering head; a second bone anchor having a second tethering head; a first staple having a first peripheral channel, and a first aperture adapted and configured to receive therethrough said first bone anchor; a second staple having a second peripheral channel, and a second aperture adapted and configured to receive therethrough said second bone anchor; a first flexible connector coupled to said first tethering head and to said second tethering head; and a second flexible connector coupled to the first peripheral channel of said first staple and to the second peripheral channel of said second staple.

B. An apparatus for attaching two bones to one another, comprising: a first flexible connector having substantially no resistance to compression; a second flexible connector having substantially no resistance to compression; a first means for anchoring said first flexible connector to a bone; a second means for anchoring said first flexible connector to a bone; a third means for anchoring said second flexible connector to a bone, said third means and said first means each being adapted and configured to structurally couple together at a first site of a first bone; and a fourth means for anchoring said second flexible connector to a bone, said fourth means and said second means each being adapted and configured to structurally couple together at a second site of a second bone.

C. An apparatus for attaching to a bone, comprising: a tethering head having a first and second opposing arms and a partitioning feature therebetween, said first arm and said partitioning feature establishing a first pathway adapted and configured to receive a first flexible connector, said second arm and said partitioning feature establishing a second pathway adapted and configured to receive a second flexible connector; means for attaching said tethering head to a bone; and means for locking said first flexible connector in the first pathway and locking said second flexible connector in the second pathway.

D. A method for attaching two portions of bone, comprising: attaching a first flexible connector to a first site of a first bone portion, wherein the first flexible connector has a first structural characteristic; attaching the first flexible connector to a second site of a second bone portion; attaching a second flexible connector to the first site of the first bone portion, wherein the second flexible connector has a second structural characteristic, and the first structural characteristic is different than the second structural characteristic; and attaching the second flexible connector to the second site of the second bone portion.

What follows are various dependent statements, each of them combinable either separately or in combination with any of the aforementioned statements A, B, C, or D:

Which further comprises cutting one of the first flexible connector of the second flexible connector, and not cutting the other flexible connector.

Wherein one of the first flexible connector or said second flexible connector comprises a material that is substantially inelastic and the other of the first flexible connector or said second flexible connector comprises a material that is more elastic than said one flexible connector.

Wherein one of the first flexible connector or said second flexible connector has a first cross-sectional area and the other of the first flexible connector or said second flexible connector has a second cross-sectional area, and the second cross sectional area is less than the first cross-sectional area.

Wherein one of the first flexible connector or said second flexible connector has a first elasticity and the other of the first flexible connector or said second flexible connector has a second elasticity, and the second elasticity is less than the first elasticity.

Wherein one of the first flexible connector or said second flexible connector has a first ultimate tensile strength and the other of the first flexible connector or said second flexible connector has a second ultimate tensile strength, and the second ultimate tensile strength is less than the first ultimate tensile strength.

Wherein said second flexible connector comprises a splicing of the ends of two separate portions of flexible material.

Wherein said first bone anchor includes a threaded shank having a longitudinal axis and said first tethering head is coupled to said first bone anchor to permit rotation about the longitudinal axis.

Wherein said first bone anchor is pivotally coupled to said first tethering head to permit pivoting about a first lateral axis at least partly orthogonal to the longitudinal axis.

Wherein said first bone anchor is pivotally coupled to said first tethering head to permit pivoting about a second lateral axis at least partly orthogonal to the longitudinal axis.

Wherein said first staple has a rounded peripheral planform shape.

Wherein the first peripheral channel includes generally parallel top and bottom ridges that extend at least partly around the circumference of the planform shape.

Wherein the top ridge and the bottom ridge each have a cutout section, and the top cutoff section is located above the bottom cutout section.

Wherein said first flexible connector has a first tensile strength, said second flexible connector has a second tensile strength, and the first tensile strength is greater than the second tensile strength.

Wherein said first flexible connector has a first elasticity in tension, said second flexible connector has a second elasticity in tension, and the first elasticity is greater than the second elasticity.

Wherein said first anchoring means includes a tethering head having a pathway adapted and configured to receive therein said first flexible connector and including a locking member to compress said first flexible connector within the pathway.

Wherein said first means includes a first threaded bone anchor and said second means includes a second threaded bone anchor.

Wherein said first means includes one pathway adapted and configured to receive there a portion of said first flexible connector, and said third anchoring means is another pathway in said first means adapted and configured to receive therein a portion of said second flexible connector.

Wherein said first means includes a first locking member to compress said first flexible connector within the one pathway and to compress said second flexible connector within the other pathway.

Wherein said first means includes a first locking member to compress said first flexible connector within the one pathway and a second locking member to compress said second flexible connector within the other pathway.

Wherein said first means includes a first bone plate and said second means includes a second bone plate.

Wherein said first means includes one pathway adapted and configured to receive there a portion of said first flexible connector, and said third anchoring means is another pathway in said first means adapted and configured to receive therein a portion of said second flexible connector.

Wherein said first means includes a first locking member to compress said first flexible connector within the one pathway and to compress said second flexible connector within the other pathway.

Wherein said first means includes a first locking member to compress said first flexible connector within the one pathway and a second locking member to compress said second flexible connector within the other pathway.

Wherein said attaching means attaches said tethering head to a bone along an attachment axis.

Wherein the attachment axis is located between the first pathway and the second pathway.

Wherein the attachment axis is located closer to the first pathway than the second pathway.

Wherein the attachment axis is aligned with the first pathway and spaced apart from the second pathway.

Wherein said means for attaching is a bone screw.

Wherein said means for attaching is a plate.

Wherein said means for attaching is a strap.

Wherein said means for attaching is a staple having a plurality of projections adapted and configured for penetration into the surface of a bone.

Wherein said first and second opposing arms are threaded, and said locking means is a set screw threadably coupled to each threaded arm, said set screw compressing each flexible connector in its respective pathway.

Wherein said first arm and said partitioning feature each have a threaded facing wall forming a first threaded receptacle, said second arm and said partitioning feature each have a threaded facing wall forming a second threaded receptacle, and said means for locking includes a first set screw receivable in the first receptacle and a second set screw receivable in the second receptacle.

Wherein said first pathway and said second pathway are parallel.

Wherein said first pathway and said second pathway are not parallel.

Wherein the first site has a first attachment axis, the second site has a second attachment axis, the first axis being spaced apart from the second axis, and said first flexible connector extends along a first direction that intersects the first axis and the second axis, and the second flexible connector extends along a second direction that intersects the first axis and the second axis.

Wherein the first site has a first attachment axis and a first radius about the first axis, the second site has a second attachment axis and a second radius about the second axis, the first axis being spaced apart from the second axis, and said first flexible connector extends along a first direction that intersects the first axis and the second axis, and the second flexible connector extends along a second direction that is tangent to the first radius and tangent to the second radius.

Wherein the structural characteristic is ultimate strength, said first flexible connector has a first ultimate strength, said second flexible connector has a second ultimate strength, and the first ultimate strength is different than the second ultimate strength.

Wherein the structural characteristic is stiffness, said first flexible connector has a first stiffness, said second flexible connector has a second stiffness, and the first stiffness is different than the second stiffness.

Wherein the structural characteristic is cross sectional area, said first flexible connector has a first cross sectional area, said second flexible connector has a second cross sectional area, and the first cross sectional area is different than the second cross sectional area.

Wherein the structural characteristic is material, said first flexible connector comprises a first material, said second flexible connector comprises a second material, and the first material is different than the second material.

Wherein the structural characteristic is tension, the first degree of tension is greater than zero, and the second degree of tension is greater than zero.

Wherein the structural characteristic is tension, and the first degree of tension is about zero.

Wherein the first bone portion is a vertebra and the second bone portion is a second vertebra.

Wherein said attaching a first flexible connector to a first site is proximate to the bone surface, said attaching a first flexible connector to a second site is proximate to the bone surface, said attaching a second flexible connector to a first site is spaced apart from the bone surface, and said attaching a second flexible connector to a second site is spaced apart from the bone surface.

Wherein said attaching a first flexible connector to a first site is spaced apart from the bone surface, said attaching a first flexible connector to a second site is spaced apart from the bone surface, said attaching a second flexible connector to a first site is proximate to the bone surface, and said attaching a second flexible connector to a second site is proximate to the bone surface.

It should be appreciated that although some embodiments are explicitly described herein in the context of dual tethers, other embodiments may include any number of tethers. The inventions are not limited to two only tethers unless expressly so stated in the claims.

While the inventions have been illustrated and described in detail in the drawings and foregoing description, the same is to be considered as illustrative and not restrictive in character, it being understood that only certain embodiments have been shown and described and that all changes and modifications that come within the spirit of the inventions are desired to be protected.

What is claimed is:

1. An apparatus for coupling a first bone portion to a second bone portion, the apparatus comprising:
   a first flexible connector;
   a second flexible connector;
   a first bone anchor including a first tethering head, said first tethering head being configured to receive a first portion of said first flexible connector;
   a second bone anchor including a second tethering head, said second tethering head being configured to receive a second portion of said first flexible connector;
   a third bone anchor defining a first aperture, said first aperture being configured to receive therethrough said first bone anchor, said third bone anchor defining a first peripheral channel, said first peripheral channel being configured to receive a first portion of said second flexible connector; and
   a fourth bone anchor defining a second aperture, said second aperture being configured to receive therethrough said second bone anchor, said fourth bone anchor defining a second peripheral channel, said second peripheral channel being configured to receive a second portion of said second flexible connector.

2. The apparatus of claim 1, wherein a first one of said first flexible connector and said second flexible connector is configured to be substantially inelastic and a second one of said first flexible connector and said second flexible connector is configured to be substantially elastic.

3. The apparatus of claim 1, wherein a first one of said first flexible connector and said second flexible connector has a first substantially uniform cross-sectional area, a second one of said first flexible connector and said second flexible connector has a second substantially uniform cross-sectional area, and said second substantially uniform cross sectional area is significantly less than said first substantially uniform cross-sectional area.

4. The apparatus of claim 1, wherein a first one of said first flexible connector and said second flexible connector is configured to have a first tensile elasticity, a second one of said first flexible connector and said second flexible connector is configured to have a second tensile elasticity, and said second tensile elasticity is significantly less than said first tensile elasticity.

5. The apparatus of claim 4, wherein said first bone anchor includes a threaded shank having a longitudinal axis, said first tethering head is configured to rotatively couple to said first threaded shank, and said first tethering head is configured to be rotated relative to said threaded shank about said longitudinal axis.

6. The apparatus of claim 5, wherein said threaded shank is configured to pivotally couple to said first tethering head, said first tethering head is configured to be pivoted relative to said first threaded shank about a first lateral axis, and said first lateral axis is generally orthogonal to said longitudinal axis.

7. The apparatus of claim 6, wherein said first tethering head is configured to be pivoted relative to said first threaded shank about a second lateral axis, and said second lateral axis is generally orthogonal to said longitudinal axis.

8. The apparatus of claim 7, wherein said third bone anchor includes a collar portion having a rounded peripheral planform shape, said first peripheral channel includes a pair of generally parallel ridges, and said pair of generally parallel ridges extends at least partly around a circumference of said planform shape.

9. The apparatus of claim 5, wherein said third bone anchor includes a collar portion having a rounded peripheral planform shape, said first peripheral channel includes a pair of generally parallel ridges, and said pair of generally parallel ridges extends at least partly around a circumference of said planform shape.

10. The apparatus of claim 5, wherein said first peripheral channel includes an eyelet.

11. The apparatus of claim 1, wherein a first one of said first flexible connector and said second flexible connector is configured to have a first ultimate tensile strength, a second one of said first flexible connector and said second flexible connector is configured to have a second ultimate tensile strength, and said second ultimate tensile strength is significantly less than said first ultimate tensile strength.

12. The apparatus of claim 1, wherein said second flexible connector includes a first member and a second member, said first member includes said first portion of said second flexible connector, said second member includes said second portion of said second flexible connector, and said first member is configured to be spliced to said second member.

* * * * *